US00PP18645P2

(12) United States Plant Patent
Zary

(10) Patent No.: US PP18,645 P2
(45) Date of Patent: Mar. 25, 2008

(54) HEDGE ROSE PLANT NAMED 'JACSHLAV'

(50) Latin Name: *Rosa hybrida*
Varietal Denomination: JACshlay

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/585,412

(22) Filed: Oct. 23, 2006

(51) Int. Cl.
*A01H 5/00* (2006.01)

(52) U.S. Cl. ..... Plt./102
(58) Field of Classification Search ..... Plt./102
See application file for complete search history.

*Primary Examiner*—Kent Bell
*Assistant Examiner*—S. B. McCormick-Ewoldt
(74) *Attorney, Agent, or Firm*—Klarquist Sparkman LLP

(57) ABSTRACT

Hedge rose plant having erect, vigorous growth habit; fragrant flowers; attractive lavender flower color; ease of propagation using softwood or hardwood cuttings and resistance to powdery mildew and rust.

1 Drawing Sheet

Figure 1:
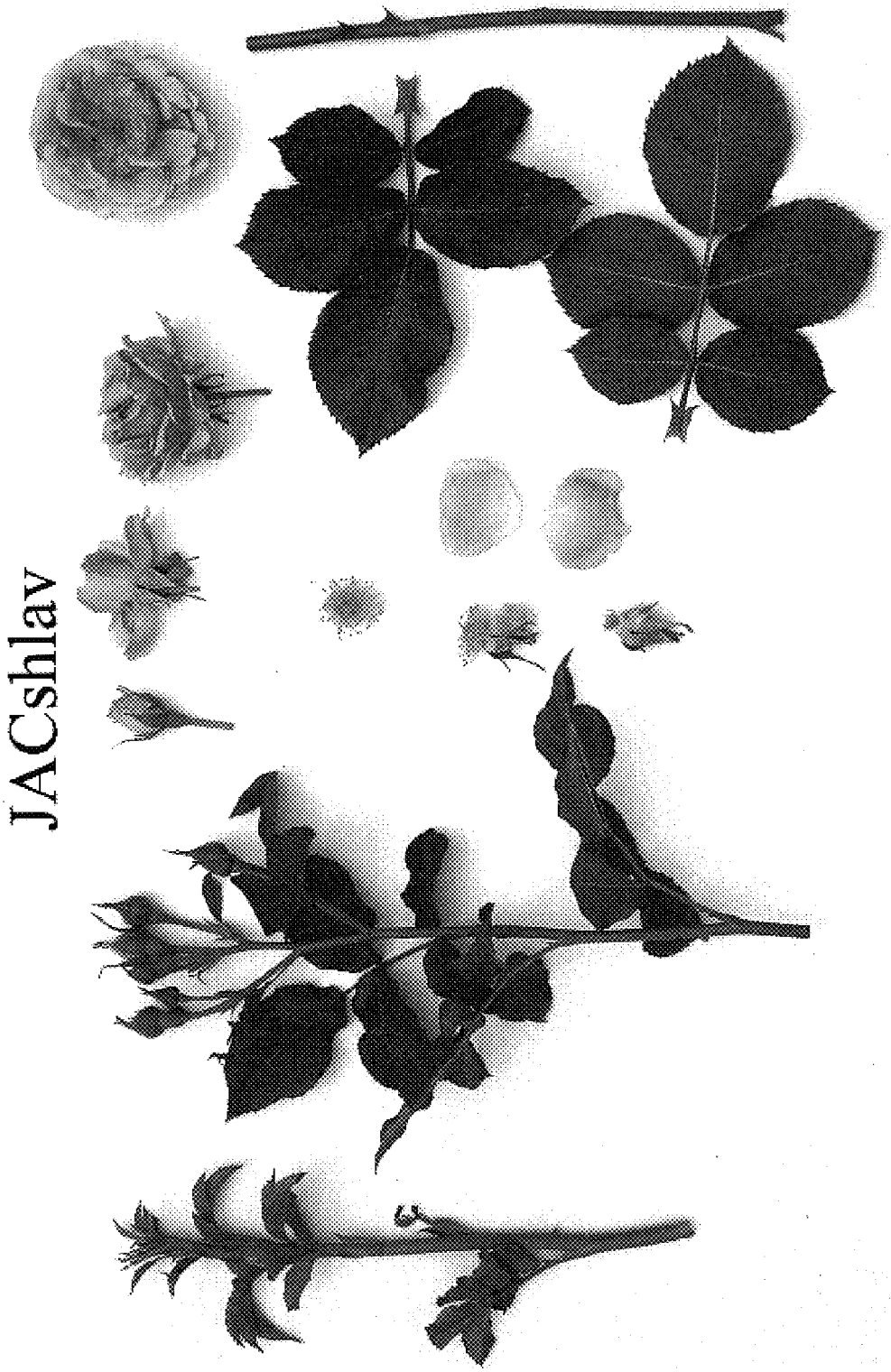

Genus and species: *Rosa hybrida.*
Variety denomination: 'JACshlav'.

ORIGIN OF THE INVENTION

The present invention relates to a new and distinct variety of a hedge rose plant named 'JACshalv' which was originated by me by crossing an unnamed seedling (unnamed seedling×unnamed seedling) (unpatented) with an unnamed seedling (unpatented) ('JACship [PP7948]×unnamed seedling).

BACKGROUND OF THE INVENTION

The primary objective of this breeding was to produce a new hedge rose variety having lavender flowers, strong fragrance, ease of propagation from hardwood cuttings, strong vigorous growth and resistance to the common fungal diseases of roses.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Erect, vigorous growth habit.
2. Fragrant flowers.
3. Attractive lavender flower color.
4. Ease of propagation using softwood or hardwood cuttings.
5. Resistance to powdery mildew and rust.

Asexual reproduction of this new variety by cuttings (both hardwood and softwood), as performed at Wasco and Somis, Calif., shows that the foregoing and all other characteristics and distinctions come true to form and are established and transmitted through succeeding propagations.

COMPARISON WITH PARENTS

The seed parent has 15 petals versus 30 petals in 'JACshlav' and has a much lighter lavender flower color. 'JACshlav' has much more fragrance and is much taller and has much larger flowers than the pollen parent.

COMPARISON WITH SIMILAR VARIETY

Other lavender flower colored roses lack the very tall, erect, almost columnar growth and excellent own root characteristics of 'JACshlav'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed seedling (unnamed seedling× unnamed seedling) (unpatented).

*Pollen parent.*—Unnamed seedling (unpatented) ('JACship' [PP7948]×unnamed seedling).

Observations made from January 2005 to September 2006 from plants commencing at two years of age grown in a garden environment at Somis, Calif.

FLOWER

Blooming habit: Continuous.

Bud:

*Size.*—About 22–26 mm long and 15–18 mm in diameter when the petals start to unfurl.

*Form.*—The bud form is pointed ovoid.

*Color.*—When sepals first divide, bud color is mainly Purple Group 77D, with Violet Group 85D at base. When half blown, the upper sides of the petals are Violet Group 85C and the lower sides of the petals are Violet Group 85C with shades of Purple Group 77D.

*Sepals.*—Color: Upper surface: Greyed-Green Group 191B, overlaid with Greyed-Green Group 196D. Lower surface: Green Group 143A with Yellow-Green Group 144B vein through the center. Length: 22–25 mm. Width: 8–10 mm. Shape: Subulate. Surface texture: Upper: Hoary. Lower: Coriaceous with some glands. There are three normally appendaged sepals. There are two unappendaged sepals with hairy edges.

*Receptacle.*—Color: Green Group 143B. Shape: Pear. Size: Medium, about 8 mm long×7 mm wide. Surface: Hairy, ciliolate.

*Peduncle.*—Length: Medium, averaging about 4–8 cm. Surface: Glandular. Color: Green Group 143B. Strength: Stiff, erect.

Bloom:

*Size.*—Medium. Average open diameter is about 6–8 cm.

*Borne.*—In pyramidal clusters of 5–9 blooms.

*Stems.*—Strength: Normal. Average length is about 25–30 cm with a diameter of 6–8 mm.

*Form.*—When first open: High centered. Permanence: Outer petals curl slightly.

*Petalage.*—Number of petals under normal conditions: 30.

*Color.*—The upper sides of the petals are Violet Group 85C. The reverse sides of the petals are Violet Group 85C with shades of Purple Group 77D. The base of the petals is Yellow Group 12C. The major color on the upper sides is Violet Group 85C.

*Variegations.*—None observed.

*Discoloration.*—The general tonality at the end of the first day: Violet Group 85C. At the end of the third day: Violet Group 85C. Further aging: By day 5, the color fades to Violet Group 85D and petals drop by day 7.

*Fragrance.*—Strong, citrus.

Petals:

*Texture.*—Moderately thick.

*Shape.*—Obdeltoid.

*Surface.*—Smooth.

*Margin.*—Smooth. Apex Shape: Emarginate. Base Shape: Cuneate.

*Form.*—Tips slightly recurved.

*Arrangement.*—Imbricated.

*Petaloids.*—Number: 3–5. Color: Violet Group 85C.

*Persistence.*—Petals drop off cleanly before drying.

*Lastingness.*—On the plant: Fair (about 7 days). As a cut flower: Fair (about 9 days).

Reproductive parts:

*Stamens.*—Number: 120–140. Length: 9 mm. Anthers: Length: 2 mm. Color: Yellow-Orange Group 16C edged with Greyed-Orange Group 168C. Arrangement: Regular around styles. Filaments: Color: Greyed-Yellow Group 160B. Length: 7 mm Pollen: Color: Greyed-Orange Group 168B.

*Pistils.*—Number: 100–120. Length: 7–10 mm. Styles: Color: Greyed-Green Group 194C at the base deepening to Red Group 47C at apex. Length: 6–9 mm. Stigmas: Color: Yellow Group 13D. Length: 1 mm.

*Hips.*—None observed.

PLANT

Form: Shrub

Growth: Very vigorous, upright, branching.

Age at maturity: Two years.

Mature plant: Height: 180 cm. Width: 120 cm.

Rootstock: Own root.

Foliage: Number of leaflets on normal mid-stem leaves: 5 or occasionally 7.

*Size.*—Medium. About 13 cm long×11 cm wide.

*Quantity.*—Abundant.

*Color.*—New foliage: Upper side: Greyed-Red Group 178C. Lower side: Greyed-Red Group 178C. Old foliage: Upper side: Green Group 139A. Lower side: Green Group 137C.

Leaflets:

*Size.*—About 50 mm long×35 mm wide.

*Shape.*—Broadly oval.

*Base shape.*—Oblique.

*Apex shape.*—Acuminate.

*Texture.*—Leathery, glossy.

*Edge.*—Smooth, serrated.

*Serrations.*—Single.

*Petiole.*—Color: Green Group 137C.

*Petiole rachis.*—Color: Green Group 137C. Underside: Smooth with an occasional prickle and glands.

*Auricles.*—None.

*Stipules.*—Length: 15–16 mm; serrated.

*Disease resistance.*—Resistant to rust and powdery mildew but susceptible to blackspot and downy mildew under normal growing conditions.

*Pest resistance.*—Not observed.

*Vein color.*—Green Group 137C.

*Venation pattern.*—Reticulate.

Wood:

*New wood.*—Color: Yellow-Green Group 146C. Bark: Smooth.

*Old wood.*—Color: Green Group 137C. Bark: Smooth.

Prickles:

*Quantity.*—On main canes from base: 6–8 per 15 cm of stem. On laterals from main canes: 6–8 per 15 cm of stem.

*Form.*—Hooked downward.

*Length.*—5–7 mm.

*Color when young.*—Greyed-Purple Group 185C.

*Color when mature.*—Greyed-Orange Group 166A.

Small prickles:

*Quantity.*—On main stalks: None. On laterals: None.

Winter hardiness: Hardy to Zone 5.

I claim:

1. A new and distinct variety of a hedge rose plant, substantially as herein shown and described, characterized particularly by its erect, vigorous growth habit; fragrant flowers; attractive lavender flower color; ease of propagation using softwood or hardwood cuttings and resistance to powdery mildew and rust.

* * * * *

UNITED STATES PATENT AND TRADEMARK OFFICE

CERTIFICATE OF CORRECTION

PATENT NO. : PP 18,645 P2
APPLICATION NO. : 11/585412
DATED : March 25, 2008
INVENTOR(S) : Zary It is certified that error appears in the above-identified patent and that said Letters Patent is hereby corrected as shown below:

On the Title Page:

Item (50) Latin Name:

"Varietal Denomination: JACshlay"

should read --Varietal Denomination: JACshlav--.

In the Specification:

Column 1, line 6, "JACshalv" should read --JACshlav--.

Signed and Sealed this

Tenth Day of March, 2009

JOHN DOLL
*Acting Director of the United States Patent and Trademark Office*